(12) United States Patent
Heskestad

(10) Patent No.: US 6,779,413 B1
(45) Date of Patent: Aug. 24, 2004

(54) CLEAN ROOM FIRE SIMULATION

(75) Inventor: Gunnar Heskestad, Dover, MA (US)

(73) Assignee: FM Global Technologies LLC, Johnston, RI (US)

( * ) Notice: Subject to any disclaimer, the term of this patent is extended or adjusted under 35 U.S.C. 154(b) by 0 days.

(21) Appl. No.: 10/379,824

(22) Filed: Mar. 6, 2003

(51) Int. Cl.[7] .............................................. G01N 17/00
(52) U.S. Cl. ................................................. 73/865.6
(58) Field of Search ........................... 73/865.6, 865.9, 73/1.06, 1.07

(56) References Cited

U.S. PATENT DOCUMENTS 6,174,469 B1 * 1/2001 Ganan-Calvo ............... 264/12

* cited by examiner

*Primary Examiner*—Robert R. Raevis
(74) *Attorney, Agent, or Firm*—Venable LLP; John P. Shannon

(57) ABSTRACT

In a fire simulation system, a fire in a clean room is simulated. A material of the type that would burn in the clean room fire is burned in a burn cell and air and combustion products are circulated through the burn cell and a secondary exposure cell in parallel. Clean room filters are provided at the top of the burn cell and the secondary exposure cell and both cells have perforated floors. A primary exposure loop may also be connected in the circulation system to receive unfiltered air and combustion products from the bum cell. The material and/or equipment to be tested for fire damage is placed in the secondary exposure cell and/or the primary exposure loop for a predetermined time and then is removed from the cell and exposed to a controlled humidity. Following the controlled humidity exposure, the material and/or equipment is evaluated for damage.

16 Claims, 1 Drawing Sheet

CLEAN ROOM FIRE SIMULATION

This invention relates to clean room fire simulation for the purpose of measuring damage to material in the clean room due to a clean room fire as a function of the material of the fire source and contaminant concentration.

A fire in a clean room, with downcast air flow from ceiling toward the floor, usually involves two contamination zones of combustion products that can damage process equipment and product, primarily by particle deposition and corrosion. A primary contamination zone, where the smoke contaminant concentration is very high, is in the immediate volume surrounding a fire. In the primary contamination zone the combustion products come into contact with the material or equipment being damaged without the combustion products being filtered. The primary contamination zone is confined by the walls of the clean room bay, or if the fire is in a large clean room bay, the primary zone extends to a surrounding umbrella-shaped boundary created by the interaction of the downcast flow in the clean room bay with the fire. A secondary contamination zone consists of a clean space surrounding the primary zone. The secondary contamination zone receives fire contaminants circulating from the primary zone but the combustion products containing the contaminants will have passed through high-efficiency particulate air filters (HEPA) or ultra-low penetration air filters (ULPA). The filters will remove most of the particulate contamination as well as gases adhering to the particles, but residual contamination in the secondary contamination zone may still be capable of causing damage. Currently there is no method or apparatus which will directly evaluate the damage potential in either the primary contamination zone or the secondary contamination zone for fires in clean room facilities and there is a need to make such evaluations as a function of the different types of materials which may be burned in a clean room fire as well as the contamination concentration in the combustion products.

SUMMARY OF THE INVENTION

In accordance with the invention, a simulator is provided comprising a burn cell and a secondary exposure cell representing the secondary contamination zone for a clean room fire. The cells may be cubical in shape and are reduced in size relative to the clean room in which a fire is being simulated. A clean room filter, such as a HEPA or ULPA filter, caps each cell and both cells have perforated floors. A fire burning a selected candidate material is provided in the burn cell and the material or equipment to be evaluated for damage is provided in the secondary exposure cell. An air mover, such as a fan or jet pump, is connected by ducting to the cells to circulate combustion products from the fire in the burn cell through the filters, downwardly through both cells, and out through the perforated floors in the cells. The downward flow through the cells simulates the downward flow that exists in a clean room. After a predetermined period allowing the combustion products from the burn cell to circulate through both the burn cell and secondary exposure cell, the damage to the material or equipment in the secondary exposure cell is evaluated to provide a determination of the damage in a secondary contamination zone of a clean room fire from the burning of the candidate material. Equipment and material could also be placed in the burn cell to evaluate the damage in the primary contamination zone of a clean room fire, but exposure conditions in the burn cell will be quite nonuniform.

To provide simulation to measure damage in a primary contamination zone of a clean room fire, the gases containing the combustion products flowing through the perforated floor of the burn cell are directed by the ducting to a test loop in which test material or equipment to be evaluated for damage is placed. The test loop contains an orifice and a mixing duct to provide a uniform exposure and contaminant concentrations at the test material or equipment in the mixing duct. The resulting damage to the material or equipment in the mixing duct will be uniform and will be an accurate indication of the damage that would occur in a primary contamination zone of a clean room fire burning the candidate material.

DESCRIPTION OF THE PREFERRED EMBODIMENTS

Figure 1:
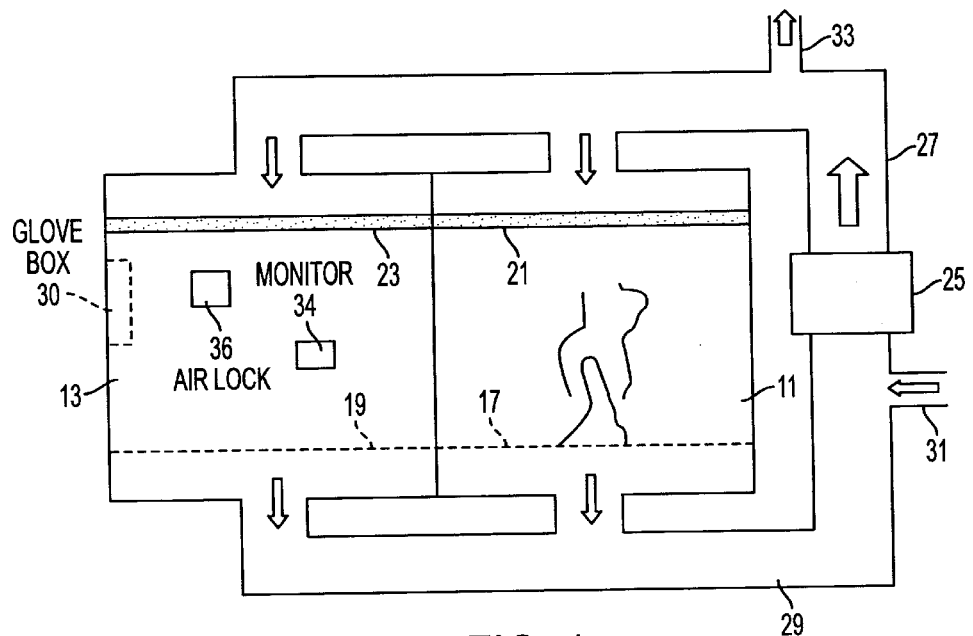
FIG. 1 is a schematic illustration of a clean room fire simulator in accordance with the invention.

The clean room fire simulator embodiment shown in FIG. 1 comprises a burn cell 11 and a secondary exposure cell 13 positioned side by side. Each of the cells 11 and 13 is generally cubical in shape having metal side walls made of steel or aluminum and perforated floors 17 and 19 also made out of steel or aluminum. The ceiling walls 21 and 23 of the cells comprise clean room filters such as HEPA or ULPA filters. In a preferred specific embodiment, the cells 11 and 13 have a vertical dimension of a little less than one meter, but they may be larger or smaller. In any case, the cells are substantially smaller than the clean room contamination zones that they simulate. An air mover 25, such as a fan or a jet pump, has its downstream side connected through duct 27 to circulate air and gases into the cells 11 and 13 through the filters 21 and 23, respectively, and out of the cells through perforated floors 17 and 19. A duct 29 connects the bottom of the cells 11 and 13 to the upstream side of the air mover 25 so that air flowing out of the cells through the perforated floors is returned to the air mover 25 to be continuously circulated through the cells. In this manner air flow in the downward direction is provided in the cells 11 and 13 to simulate the downward flow that occurs in a clean room. The flow velocity provided in the cells by the air mover in the preferred specific embodiment is about 0.3 meters per second but can be higher or lower. If the air mover is a fan, the fan is of a design which is easily cleanable. A jet pump, which is intrinsically easily cleanable, may be used as the air mover instead of the fan. Filtered air is provided in the circulation system through inlet 31 to replace air flow diverted to a throttled discharge 33 to the circulation system. The inlet 31 and the throttled discharge 33 are used to control the operating pressure in the circulation system to be slightly greater than atmospheric pressure and to clear the apparatus of smoke and combustion gases after a test. If the air mover 25 is in the form of a jet pump, which is run on filtered air, the filtered air driving the jet pump will provide sufficient make-up air so that the inlet 31 is not needed.

To run a test for fire damage in a secondary contamination zone from a clean room fire for a selected candidate material being burned, the selected candidate material is placed in the burn cell 11 and ignited. The material or equipment to be evaluated for damage is placed in the secondary exposure cell 13. The air mover 25 is operated to provide air flow through both of the cells 11 and 13 in parallel so that the combustion products from the fire in the burn cell 11 are circulated through the burn cell and the secondary exposure cell 13 to expose the material or equipment in the secondary exposure cell 13 to contamination. The initial temperature and relative humidity in the cells 11 and 13 and the circulation system prior to the fire in the burn cell being ignited are controlled to correspond to typical values for these conditions in a clean room. While the fire burns and the combustion products are circulated, the changes in the temperature in the cells and in the relative humidity will correspond to changes that occur in these parameters in a real clean room fire. To monitor contaminant concentration in the simulation, the concentration of a tracer such as fire generated carbon dioxide is measured in cell 13 by monitor 34. The temperature, the relative humidity, and the concentration of various gases may also be measured by additional monitors in the cells 11 and 13 for diagnostic purposes. The circulation through the cells 11 and 13 is continued for a selected period while the fire burns in the burn cell 11. After the test, the contaminated materials and/or equipment is moved out of the exposure cell and is exposed to a controlled humidity environment in a separate cell, whereupon the contamination and corrosion and other damage to the material and/or equipment is evaluated.

Material and equipment to be evaluated for damage are moved in and out of the cell 13 through an air lock 36 by means of a glove box 30 to avoid incidental contamination of the materials or equipment.

Figure 2:
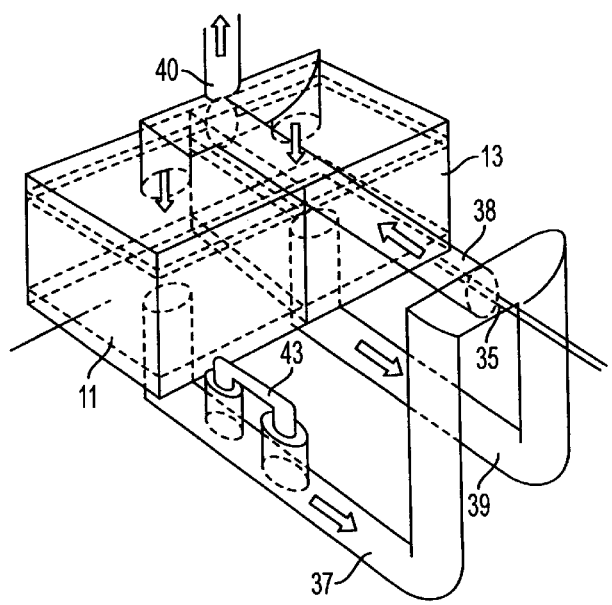
FIG. 2 illustrates an alternative embodiment provided with a capability for accurately measuring the damage in the primary contamination zone as well as the secondary contamination zone.
Figure 3:
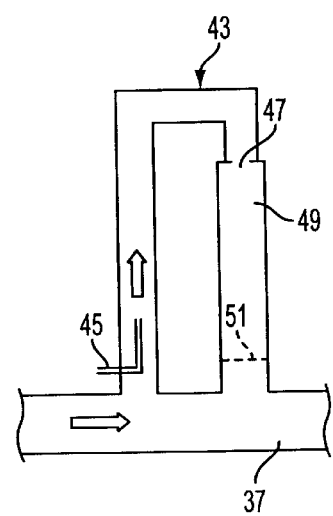
FIG. 3 is an elevational view of the portion of the simulator of FIG. 2 for measuring the damage in the primary contamination zone.

Some measure of the fire damage in the primary contamination zone may be determined by placing material samples to be tested for damage in the burn cell 11 in the same manner that damage is tested for in the secondary exposure cell 13. However, exposure conditions in the burn cell 11 will be quite nonuniform. To obtain a more accurate and reliable evaluation of damage in the primary contamination zone, an apparatus like that shown in FIGS. 2 and 3 is used. The apparatus shown in FIG. 2 comprises a burn cell 11 and a secondary exposure cell 13 having perforated floors and ceiling walls in the form of filters employed in a manner similar to the system shown in FIG. 1. In the embodiment of FIGS. 2 and 3, a duct 37 receives air and combustion products circulated through the perforated floor of the burn cell 11 and directs the flow to the inlet of duct 38. Duct 39 receives air and combustion products circulated through the perforated floor of the secondary exposure cell 13 and directs this flow to the inlet of the duct 38, which directs the air and combustion products into the cells 11 and 13 through the filters at the tops of the cells. The flow circulation is caused by a jet pump 35 which directs a jet of air into the inlet of the duct 38. Excess air and combustion products in the circulation system are diverted through throttled discharge 40. The secondary exposure cell 13 in FIG. 2 will enable evaluation of damage in the secondary contamination zone in the same manner as the secondary exposure cell in the system illustrated in FIG. 1 enables such evaluation. To obtain an accurate evaluation of damage in the primary contamination zone, a test circulation loop 43 is connected to receive a portion of the combustion product flow in the duct 37 circulated through the loop 43 and then returned to the duct 37. As shown in FIG. 3 the loop has a jet pump 45 arranged to direct a jet of air into the inlet side of the loop to draw a portion of the combustion products in the duct 37 into the loop 43. The inlet side of the loop 43 leads to an orifice 47 at the top of mixing duct 49 serving as a primary exposure zone. A primary exposure site 51 for receiving test materials and/or equipment is provided in the mixing duct 49 spaced downstream from the orifice 47 so that uniform exposure to the combustion products is achieved. The flow velocity past the sample or samples at the site 51 is preferably the same as that in the secondary exposure cell 13, 0.3 meters per second. As in the case of the exposure cell 13, the flow velocity past the exposure site 51 can be higher or lower than 0.3 meters per second. The exposure site 51 is located at a distance downstream from the mixing orifice 47 equal to 5 to 6 diameters of the mixing duct, to assure thorough mixing of the combustion products prior to their contact with the material and/or equipment placed at the exposure site 51. Since the combustion products entering the mixing duct 49 are unfiltered, the contamination and corrosion damage to the test samples at the site 51 will correspond to the damage that would occur in a clean room fire in the primary contamination zone. Because the combustion products are thoroughly mixed by flowing through the orifice 47 and the mixing duct, the contamination damage at the exposure site 51 will be uniform. The cells 11 and 13 in the embodiment of FIGS. 2 and 3 are provided with tracer monitors (not shown) like the cell 13 in the system of FIG. 1. In the system of FIGS. 2 and 3, like the system of FIG. 1, the materials and/or equipment being tested is exposed to a controlled humidity environment before the damage to the material and/or equipment is evaluated.

By burning different candidate materials, which might be the source of a fire in a clean room in the burn cell 11, the damage caused by the burning of these different materials can each be evaluated separately with the apparatus and method described above.

Damage measurement on the test material or equipment for various tracer concentration histories and post test exposures, together with tracer dispersion patterns and concentrations that would occur in a clean room fire, obtained, for example, from computer modeling, can be used to determine the potential extent of the ultimate damage in the field from clean room fires involving the tested materials.

The above description is of preferred embodiments of the invention and modifications may be made thereto without departing from the spirit and scope of the invention, which is defined in the appended claims.

What is claimed is:

1. A clean room fire simulation system comprising a burn cell adapted to burn material therein, a secondary exposure cell adapted to have material or equipment to be evaluated for damage placed therein, a circulation system arranged to circulate air and combustion products from said burn cell through said secondary exposure cell, a clean room filter arranged to filter the air and combustion products as they enter said secondary exposure cell, and a monitor in said secondary exposure cell for monitoring the concentration of a predetermined gas generated by the burning of the material in said burn cell.

2. A simulator as recited in claim 1 wherein said circulation system circulates air and combustion products through said burn cell in parallel with the circulation of air and combustion products through said secondary exposure cell, and a clean room filter is positioned to filter the air and combustion products circulated into said burn cell.

3. A clean room fire simulation system as recited in claim 1 wherein said predetermined gas is carbon dioxide.

4. A clean room fire simulation system as recited in claim 1 wherein said burn cell and said secondary exposure cell are substantially smaller than a clean room exposure zone.

5. A clean room fire simulation system as recited in claim 1 wherein said circulation system is arranged to cause air and combustion products to flow downwardly through said secondary exposure cell.

6. A clean room fire simulation system as recited in claim 5 wherein the floor of said secondary exposure cell is perforated to permit air and gases to flow through the floor of said secondary exposure cell as it circulates.

7. A clean room fire simulation system as recited in claim 1 wherein said circulation system includes a duct immediately downstream from said burn cell arranged to receive air and unfiltered combustion products from the burning of material in said burn cell, and further comprising a loop connected to said duct and arranged to have some of the air and unfiltered combustion products in said duct to pass through said loop, an exposure site contained in said loop adapted to receive material or equipment to be evaluated for damage and to be contacted by air and combustion products passing through said loop.

8. A clean room fire simulation system as recited in claim 7 wherein said loop includes a mixing duct having a mixing orifice at the upstream end thereof, said exposure site being in said mixing duct spaced from said orifice downstream from said mixing orifice.

9. A clean room fire simulation system as recited in claim 7 wherein said loop is arranged to return the air and combustion products passing through said loop to said duct.

10. A clean room fire simulation system comprising a burn cell adapted to burn material therein, a secondary exposure cell adapted to have a material or equipment to be tested for damage placed therein, a circulation system arranged to circulate air and gas through said burn cell and said secondary exposure cell in parallel, clean room filters arranged to filter the air and combustion products circulated through said burn cell and said secondary exposure cell, said circulation system including a duct immediately downstream from said burn cell to receive unfiltered combustion products from the burning of material in said burn cell, a loop connected to said duct and arranged to have some of the air and unfiltered combustion products in said duct pass through said loop, an exposure site in said loop adapted to receive material and/or equipment to be evaluated for fire damage and arranged to be brought into contact with the combustion products in said loop.

11. A clean room fire simulation system as recited in claim 10 wherein said loop includes a mixing duct having a mixing orifice at the upstream end thereof, said exposure site being in said mixing duct spaced from said orifice downstream from said mixing orifice.

12. A clean room fire simulation system as recited in claim 10 wherein said loop is arranged to return the air and combustion products passing through said loop to said duct.

13. A method of evaluating damage from a clean room fire comprising selecting a material which may be burned in a clean room fire, burning said material in a burn cell, placing a test material or equipment in a secondary exposure cell, circulating air and combustion products from said burn cell through a clean room filter and then through said secondary exposure cell to expose said test material and/or equipment to said combustion products and evaluating the damage to said test material and/or equipment.

14. A method as recited in claim 13 further comprising exposing said test material and/or equipment to a controlled humidity after said test material and/or equipment has been exposed to said combustion products but before the evaluation of said test material and/or equipment for damage.

15. A method as recited in claim 13 wherein said air and said combustion products are circulated through said burn cell and said secondary exposure cell in parallel, wherein the circulated air and combustion products pass through a clean room filter before entering said burn cell.

16. A method as recited in claim 13 wherein air and unfiltered combustion products from the burning of the material in said burn cell are passed through a chamber containing a second test material and/or equipment to be tested for damage, and evaluating said second test material and/or equipment for damage.

\* \* \* \* \*